United States Patent [19]

Seney

[11] Patent Number: 5,236,419

[45] Date of Patent: Aug. 17, 1993

[54] PAIN-ALLEVIATING DEVICE FOR INJECTING HYPODERMIC NEEDLES

[76] Inventor: John S. Seney, Box 152, Sugarloaf Shores, Fla. 33044

[21] Appl. No.: 989,575

[22] Filed: Dec. 11, 1992

[51] Int. Cl.5 .............................................. A61M 5/00
[52] U.S. Cl. ................................................... 604/112
[58] Field of Search ............... 604/112, 192, 263, 187, 604/110

[56] References Cited

U.S. PATENT DOCUMENTS

| | | | |
|---|---|---|---|
| 2,746,264 | 6/1956 | Keyes | 604/112 |
| 3,399,675 | 4/1968 | Hill | 604/112 |
| 3,483,869 | 8/1969 | Hayhurst | 604/112 |
| 3,563,239 | 11/1970 | Hill | 604/112 |
| 3,605,742 | 9/1971 | Tibbs | 604/112 |
| 3,630,192 | 1/1972 | Jamshidi | 604/112 |
| 4,725,265 | 3/1988 | Sairenji | 604/112 |

Primary Examiner—John D. Yasko
Attorney, Agent, or Firm—C. Harcus Just

[57] ABSTRACT

A pain-alleviating device for injecting a hypodermic needle into human flesh comprising a tubular support for a syringe containing medicament and having an injection needle on one end and a plunger in the other end, the support having a canister on the end opposite that which receives the syringe and the canister comprising an annular chamber containing a solution of water and ethylene glycol or other suitable substance, such as NaCl, adapted to be frozen to as low as 0° F., the needle of the syringe being disposed safely within the chamber of the canister until the syringe is projected farther into the tubular support sufficiently to project the needle through the outer end of the canister into a skin-chilled surface on a patient abutting the outer end of the canister. The assembled support and syringe being adapted to be disposed in a sub-zero chamber to chill the solution below freezing sufficiently to lower the temperature of the body area engaged by the skin-chilling surface of the canister, whereby the raising of the temperature to the 27°-29° F. range produces heat of fusion adequate to produce a relatively constant temperature of the foregoing range for a minimum period of three minutes within which painless injection of the needle and discharge of medicament may occur by the use of such pain-alleviating device.

7 Claims, 1 Drawing Sheet

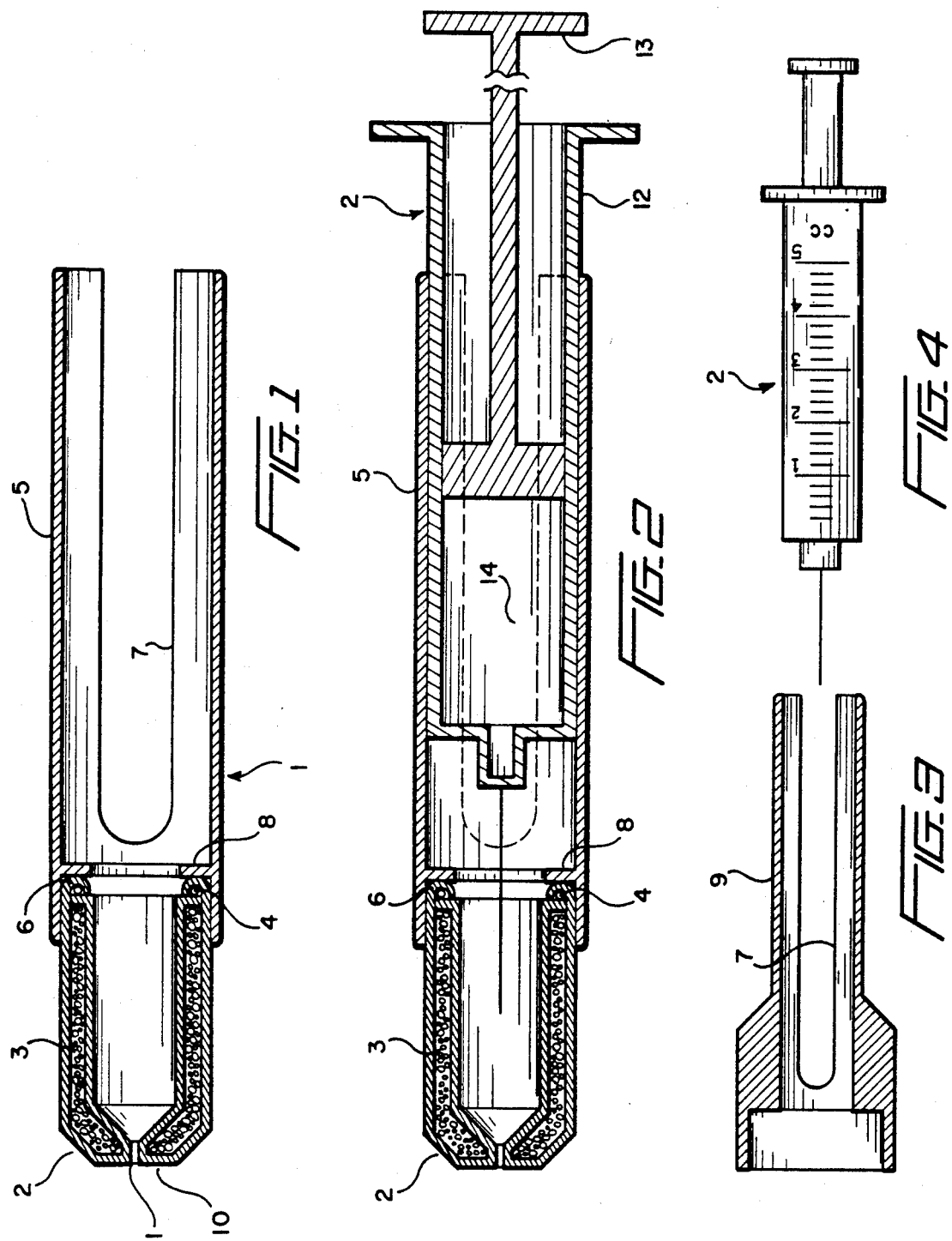

PAIN-ALLEVIATING DEVICE FOR INJECTING HYPODERMIC NEEDLES

BACKGROUND OF THE INVENTION

The concept of relieving or preventing pain by the application of cold devices is commonplace. The device comprising this invention takes this proven and widely-used pain-alleviating technique and applies it to a hypodermic syringe assembly. One routine application of cold to achieve a local anesthestic effect is the use of ethyl chloride. This rapidly-evaporating chemical is sprayed on the surface of the skin to anesthetize a small area so that minor surgery operations may be performed comfortably. Such operations are performed in this manner to remove, for example, a wart, mole, or other skin growth.

The device comprising the invention does not freeze the skin but lowers the surface temperature of the skin sufficiently to act as an effective local anesthetic for needle insertion. Further, the cold is continually applied to the site during needle insertion and injection and therefore, the anesthetic effect of the cold is maintained throughout the procedure for a sufficient period of time. This is not the situation when using ethyl chloride which continues to warm once it has been applied, thereby reducing its anesthetic effects.

CITATION OF PRIOR ART

To illustrate the present state of the patent art pertaining to the present invention, the following patents are cited:

| | | |
|---|---|---|
| U.S. Pat. No. 2,746,264 - Keyes | 1956 | |
| U.S. Pat. No. 3,399,675 - Hill | 1968 | |
| U.S. Pat. No. 3,483,869 - Hayhurst | 1969 | |
| U.S. Pat. No. 3,563,239 - Hill | 1971 | |
| U.S. Pat. No. 3,630,192 - Jamshidi | 1971 | |
| U.S. Pat. No. 4,725,265 - Sairenji | 1988 | |

SUMMARY OF THE INVENTION

There are two basic scientific reasons that the device comprising the invention operates as desired. It is due to the utilization of the heat of fusion principal and the chemical reaction rate law.

The ability of the device to maintain a temperature freezing (27°–29° F.) for a reasonably extended time, such as 3 minutes or more, is due to the employment of the heat of fusion principle. This principle states that the amount of energy required to cool water is altered when water is cooled below its freezing point. For example, 1 BTU of heat per pound of water must be removed for each degree of Fahrenheit that the temperature of the water is lowered until it reaches its freezing point, 32° F. At this point, it now requires 144 BTU/lb. to freeze one pound of ice even though the temperature is just slightly below 32° F. When this process is reversed, it requires 144 BTU of heat per pound of ice to melt the ice. This is the principle of the heat of fusion. During the melting process, the temperature of the ice remains at 32° F. A Thermal Energy Storage (T.E.S.) chemical composed of distilled water and ethylene glycol or other suitable substance, such as NaCl, may be used to lower the freezing point of water below 32° F. It has been found that when a solution of approximately 6.5% ethylene glycol and 93.5% water is prepared and reduced to 0° F., it produces the desired operable heat of fusion at 27°–29° F. for a minimum period of 3 minutes.

When the device is frozen to 0° F., it is removed from the freezer. At this point, the frozen water mass will begin to warm. As the temperature of the mass approaches 27°–29° F., the steady warming rate will decrease and the mass will remain at 27°–29° F. until all the heat of fusion given off during the freezing process is absorbed back into the mass. When this occurs, the temperature of the mass will begin to rise steadily again. The period of time from when the device is removed from the freezer until all the heat of fusion is adsorbed again, is at least three minutes plus, and this amount of time is sufficient to permit comfortable and effective skin cooling and comfortable injection of medication.

The chemical reaction rate law states that a chemical reaction rate will double for every 10° C. (18° F.) temperature increase This fact, therefore, influences the ability of the reactionary chemicals that cause sensations in certain nerves to be stimulated, or not stimulated, as a function of temperature. The pain receptors in the skin are all free nerve endings. A chemical substance or substances released from the cells or formed in damaged tissues excite the pain nerve endings. Two such substances are known to be bradykinin and histamine. Therefore, if the temperature of the skin can be reduced sufficiently, the chemical release of these substances will be significantly or completely reduced which results in little or no excitation of the pain nerve endings and therefore, reduces or eliminates the pain sensation in accordance with the chemical reaction rate law of chemistry.

BRIEF DESCRIPTION OF THE DRAWING

FIG. 1 illustrates in longitudinal section the principal element of the invention which is a tubular support which may be injection-molded from suitable plastic material and includes on one end a canister which contains the liquid solution to be frozen.

FIG. 2 illustrates in longitudinal section, the support shown in FIG. 1 with a conventional hypodermic syringe assembly positioned therein.

FIG. 3 is a longitudinal sectioned view of a different size of tubular support from that shown in FIGS. 1 and 2.

FIG. 4 is a side view of a conventional syringe having volume indicia thereon which is viewable through slots in the tubular support.

DESCRIPTION OF THE PREFERRED EMBODIMENTS OF THE PRESENT INVENTION

Referring to FIG. 1, the hypothermic hypodermic pain-alleviating device is comprised of two principal components, one is the metallic thermally-conductive canister 2, and the other is the preferably NYLON syringe-receiving preferably cylindrical support 5 or guide means 5. Canister 2 is a cylindrical unit containing a thermally energy storage (TES) solution 3, and having in one end a small hole 1 through which the needle of the hypodermic syringe is projectable. The canister 2 has on one end a skin-contact face 10. The canister 2 comprises a coaxial pair of cylindrical metal walls or shells of different diameters to form an annular space in which solution 3 is contained in leak-proof manner. The outer end of this composite pair of walls or shells is sealed and is conical in shape and terminate in the hole 1. The other end 6 of one shell is crimped over the end of the other shell and encloses an "O" ring 4 to form an airtight seal. The NYLON support 5 slidably supports the hypodermic syringe assembly 12. Annular flange stop 8 in support 5 provides an inner end of a socket which receives canister 2 tightly. The NYLON support 5 may vary in size to accommodate different sizes of hypodermic syringe, one additional size of which is shown in FIG. 3.

The TES solution 3 in canister 2 is formulated to take maximum advantage of the heat of fusion principle. Hypodermic syring assembly 12 is comprised of hypodermic needle 11, syringe body 12 and plunger 13, having a knob 15 on the outer end thereof. When the hypothermic hypodermic assembly 12 has been assembled, it is inserted into the NYLON support 5, preferably with a limited friction fit, and it is pushed inward until the tip of needle 11 comes to rest entirely inside canister 2. The skin-contact face 10 of canister 2 is then pressed against the skin where injection is to occur and is held against the skin until the desired anesthetic effect is achieved, according to a doctor's judgment.

Once sufficient cooling has occurred, the hypodermic syringe assembly 12 is pushed forward to permit needle 11 to pass through the small hole 1 of canister 2 which is located in the center of the anesthetized area, and then the needle is injected into the skin or flesh of a patient. Syringe 12 is then pushed far enough to penetrate the skin to the desired injection depth. Syringe plunger 13 is then pushed forward to dispense the medicinal fluid 14 from syringe 12 to the extent shown on a scale on the syringe as viewed in slot 7 extending longitudinally along the support 5. When the medicinal fluid 14 has been injected, the syringe assembly is withdrawn and the canister 2 and syringe 12 are removed from the injection site.

The time required to apply the support for syringe and contact face 10 to the skin prior to injection varies from approximately 10 to 30 seconds, depending upon the amount of anesthesia desired. This period is sufficient to desensitize the skin and permit comfortable insertion of the needle 11.

When the device is put in a freezer at 0° F., it will freeze and be ready to use within approximately an hour. After removal from the freezer, it is effective for use for a minimum of 3 minutes.

The device is capable of being autoclaved to temperatures up to 270° F., at 15 PSI steam pressure for periods acceptable for normal clinical autoclaving procedures The directions for use are as follows:

1. Remove the hypodermic device from the freezer,
2. Attach the proper size NYLON syringe support to the cold canister.
3. Insert the hypodermic needle and syringe assembly into the open end of the support and push the syringe inward until the tip of the needle rests just inside the small hole at the outer end of the canister.
4. Place the skin-contact end of the canister against the skin where the injection is to occur.
5. Hold the device against the skin for approximately 10 to 30 seconds or more. The longer the device is held against the skin, the greater will be the anesthetic effect.
6. When the desired cooling time has elapsed, push the plunger of the syringe assembly into the support until the required needle penetration depth is reached.
7. Inject the medication by pushing the plunger inward for a distance commensurate with the direct reading of the gage showing in one of the slots in the support for the syringe.
8. Pull the syringe back until the needle tip is inside the interior of the canister.
9. Remove the device from the patient.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A hypothermic pain-alleviating device for injecting hypodermic needles comprising, in combination, a support having on one end guide means adapted to receive a hypodermic syringe assembly for support thereof, and on the other end having a canister provided with a longitudinal passage therethrough arranged to receive in stored manner an injection needle of said syringe assembly, said canister having in an outer end a needle passage extending through a skin-contacting surface at the end opposite said guide means and said canister comprising a sealed annular chamber surrounding said longitudinal passage and containing in sealed manner a thermal energy storage solution comprising a solution of water and ethylene glycol or other suitable substance, such as NaCl, which upon initially being frozen substantially below 32° F. develops the heat of fusion of said solution to produce a substantially even temperature within said skin-contacting surface within a substantially even range of 27°-29° F. for a minimum period of time of three minutes to anesthetize the skin surface contacted by said skin-contacting surface of said canister and permit a substantially painless injection of medicament through said needle on said syringe.

2. The device according to claim 1 in which the temperature to which said solution is frozen is substantially 0° F.

3. The device according to claim 1 in which said canister comprises a pair of similarly-shaped metallic members having nested and radially-spaced apart cylindrical bodies of different diameters to provide a cylindrical space therebetween and said members at one end tapering toward a relatively small diameter needle passage and both ends of said nested members being tightly sealed in leak-proof manner.

4. The device according to claim 1 in which said support is complementary in shape to the body of said syringe which it is adapted to receive, and said support having at least one slot extending longitudinally therethrough through which volume indications on said syringe are viewable.

5. The device according to claim 1 in which said support is complementary in shape to the outer surface of said syringe and receives the same with limited friction for longitudinal slidable adjustment therein and said support at said other end having a socket which receives one end of said canister in fixed position therein, whereby said syringe may be positioned in said support with the outer end of the needle on said syringe disposed entirely within said passage in said canister for projection of the needle through said needle passage in said skin-contacting surface.

6. The device according to claim 1 in which said support is complementary in cross-section with a syringe to be slidably inserted with limited slidable friction therein, and said support having at least one longitudinal slot through which measuring indicia on the wall of a syringe may be viewed while discharging medication into the flesh of a patient.

7. The device according to claim 1 in which said solution is within the range of approximately 6.5% ethylene glycol and 93.5% water or other suitable solution, such as NaCl.

* * * * *